US00PP15110P2

(12) United States Plant Patent
Cain et al.

(10) Patent No.: US PP15,110 P2
(45) Date of Patent: Aug. 24, 2004

(54) GRAPEVINE PLANT NAMED 'SUGRATWENTYSIX'

(50) Latin Name: *Vitis vinifera*
Varietal Denomination: Sugratwentysix

(75) Inventors: David W. Cain, Bakersfield, CA (US); Michael J. Striem, Bakersfield, CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 10/618,502

(22) Filed: Jul. 10, 2003

(51) Int. Cl.[7] ..... A01H 5/00
(52) U.S. Cl. ..... Plt./207
(58) Field of Search ..... Plt./207

*Primary Examiner*—Anne Marie Grunberg
*Assistant Examiner*—June Hwu
(74) *Attorney, Agent, or Firm*—Knobbe Martens Olson & Bear, LLP

(57) ABSTRACT

A new and distinct grapevine variety characterized by producing seedless grapes that are firm and crisp, naturally medium size, green-yellow skin color, elliptic berry shape, high sugar content and excellent eating quality. The new variety 'Sugratwentysix' is a late mid-season ripening grape with an outstanding ability to hang on the vine.

1 Drawing Sheet

Latin name of the genus and species claimed: *Vitis vinifera.*
Variety denomination: 'Sugratwentysix'.

BACKGROUND AND SUMMARY OF THE INVENTION

This invention relates to the discovery and asexual propagation of a new variety of grapevine as herein described and illustrated. The new variety is characterized by producing medium sized, elliptic-shaped grapes with a green-yellow skin color. The grapes are firm and crisp, having a high sugar content and excellent eating quality.

The new variety was first hybridized by David W. Cain and Michael J. Striem in Wasco, Kern County, Calif., the variety being originated by controlled hybridization and subsequent ovule culture of seed traces and embryo rescue procedures. The seed parent is 'Sun World Seedling 86005-098-073' (unpatented) and the pollen parent is 'Sun World Seedling 85022-079-636'(unpatented). The parent varieties were first crossed in May 1990, with the date of sowing being August 1990, and the date of first flowering being August 1993. The new 'Sugratwentysix' variety was first asexually propagated by David W. Cain in January, 1994, in Wasco, Kern County, Calif., using hardwood cuttings.

The new variety, 'Sugratwentysix' is a late mid-season ripening green-yellowish seedless grape with an outstanding ability to hang on the vine. The new variety ripens about a month after the 'Thompson Seedless' grape variety, when grown in the San Joaquin Valley, Calif. The new variety is characterized by producing grapes that are firm and crisp, naturally medium size, green-yellow skin color, elliptic berry shape, high sugar content and excellent eating quality.

'Sugratwentysix' is distinguishable from its seed parent (86005-098-073) a seeded muscat selection, by being seedless and having elliptical berries and neutral in flavor. 'Sugratwentysix' is distinguishable from its pollen parent in that the pollen parent (85022-079-636) has much smaller spherical berries (about 2.6 g.) with a muscat flavor unlike those of 'Sugratwentysix', which are 3.98 g. in size and neutral in flavor.

The new variety 'Sugratwentysix' is distinguished from 'Perlette', (unpatented), 'Thompson Seedless' (unpatented) and other commonly grown white seedless grapevine varieties by possessing a very firm and crisp flesh, which gives it an exceptional eating quality.

'Sugratwentysix' most nearly resembles the 'Thompson Seedless' variety in its berry flesh and skin colors. The new variety differs from 'Thompson Seedless' in that the vine is more vigorous and less productive than the 'Thompson Seedless' variety. It also differs from the 'Thompson Seedless' variety by ripening about a month after 'Thompson Seedless' and having naturally larger and elliptic berries, with much better hanging ability on the vine as compared with 'Thompson Seedless'.

The new grapevine variety resembles the 'Sugratwentytwo' grapevine variety by berry shape and color. It differs from the 'Sugratwentytwo' variety by having a substantially earlier ripening period which is about the same time as 'Sugraeighteen'.

The new 'Sugratwentysix' variety has been shown to maintain its distinguishing characteristics through successive asexual propagations by, for example, cuttings.

BRIEF DESCRIPTION OF THE FIGURE

The accompanying photographic illustration in FIG. 1 illustrates in full color a typical cluster of berries, a young shoot, and a mature leaf blade of the new grapevine. The colors are as nearly true as is reasonably possible in a color representation of this type.

DETAILED BOTANICAL DESCRIPTION OF THE INVENTION

Figure 1:
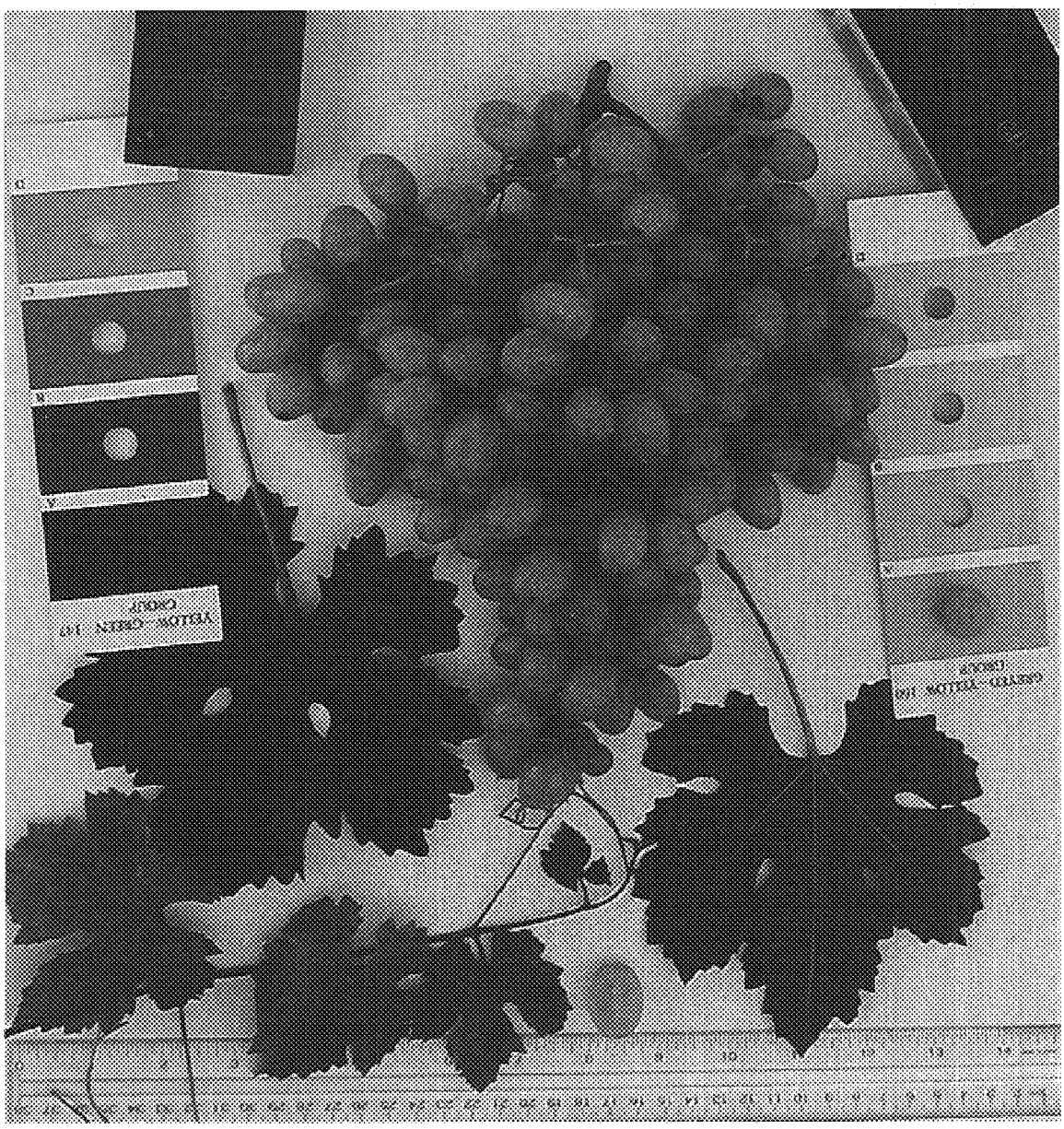

Throughout this specification, color names beginning with a small letter signify that the name of that color, as used in common speech, is aptly descriptive. Color names beginning with a capital letter designate values based upon The R.H.S. Colour Chart, published by The Royal Horticultural Society, London, England.

Many of the description values in this specification are based on and conform to those set forth by the International Board for Plant Genetic Resources Institute Grape Descriptors (Vitis spp.) of 1983 and/or 1997 which was developed in collaboration with the Office International de la Vigne et du Vin (OIV) and the International Union for the Protection of New Varieties of Plants (UPOV).

The descriptive matter which follows pertains to eight year old 'Sugratwentysix' plants grown in the vicinity of Wasco, Kern County, Calif., during 2002, and is believed to apply to plants of the variety grown under similar conditions of soil and climate elsewhere.

VINE

General:
- *Height.*—Approximately 225 cm.
- *Spread.*—Approximately 450 cm.
- *Vigor.*—Vigorous.
- *Density of foliage.*—Medium.
- *Productivity.*—Medium productive.
- *Root stock.*—Own roots.

Trunk:
- *Shape.*—Slender.
- *Diameter at approximately 25 cm from soil line.*—Approximately 141 mm.
- *Straps.*—Continuous.
- *Surface texture.*—Medium.
- *Inner bark color.*—About Greyed-orange 177C.

SHOOTS

Young shoot:
- *Form of tip.*—Wide open.
- *Distribution of anthocyanin coloration of tip.*—Piping (striped).
- *Intensity of anthocyanin coloration of tip.*—Weak.
- *Density of prostrate hairs on tip.*—Very sparse.
- *Density of erect hairs on tip.*—Very sparse.

Woody shoot (mature canes):
- *Shape.*—Stocky.
- *Internode length.*—Long — approximately 39.61 mm.
- *Width at node.*—Approximately 17.32 mm.
- *Cross section.*—Circular.
- *Surface.*—Smooth.
- *Main color.*—About Greyed-orange 166C.
- *Lenticels.*—Absent.
- *Density of erect hairs on nodes.*—None or very sparse.
- *Density of erect hairs on internodes.*—None or very sparse.
- *Growth of axillary shoots.*—Strong — approximately 30.0 cm.

Flowering shoot:
- *Vigor during flowering.*—Medium.
- *Attitude during flowering on shoots which are not tied.*—Erect.
- *Color of dorsal side of internodes.*—About Yellow-green 144B with stripes of about Greyed-purple 183B.
- *Color of ventral side of internodes.*—About Yellow-green 144B with strips of about Greyed-purple 183B.
- *Color of dorsal side of nodes.*—About Yellow-green 144A.
- *Color of ventral side of nodes.*—About Yellow-green 144A.
- *Density of erect hairs on nodes.*—Absent.
- *Erect hairs on internodes.*—Absent.
- *Density of prostrate hairs on nodes.*—Absent.
- *Density of prostrate hairs on internodes.*—Absent.
- *Anthocyanin coloration of buds.*—Absent.

Tendrils:
- *Distribution on the shoot at full flowering.*—Discontinuous.
- *Thickness.*—Medium.
- *Color.*—About Yellow-green 145A.
- *Form.*—Trifurcated.
- *Number of consecutive tendrils.*—Up to two.
- *Length of tendril.*—Medium — approximately 18 cm.

LEAVES

Young leaves:
- *Color of upper surface of first 4 distal unfolded leaves.*—Green.
- *Average intensity of anthocyanin coloration of six distal leaves prior to flowering.*—Absent or very weak.
- *Density of prostrate hairs between veins at lower surface of 4th distal unfolded leaf.*—Absent.
- *Density of erect hairs between veins at lower surface of 4th distal unfolded leaf.*—Absent.
- *Density of prostrate hairs on veins at lower surface of 4th distal unfolded leaf.*—Absent.
- *Density of erect hairs on veins at lower surface of 4th distal unfolded leaf.*—Absent.

Mature leaves:
- *Average length.*—Approximately 175 mm.
- *Average width.*—Approximately 183 mm.
- *Size of blade.*—Very large.
- *Shape of blade.*—Wedge-shaped.
- *Number of lobes.*—Three.
- *Anthocyanin coloration of main veins on the upper side of the blade.*—Absent.
- *Mature leaf profile.*—Revolute.
- *Blistering surface of blade upper surface.*—Absent.
- *Leaf blade tip.*—In the plane of the leaf.
- *Undulation of margin.*—Slight.
- *Apex.*—Cuspidate.
- *Thickness.*—Medium.
- *Undulation of blade between main and lateral veins.*—Absent.
- *Shape of teeth.*—Mixture of both sides straight and both sides convex.
- *Length of teeth.*—Medium.
- *Ratio length/width of teeth.*—Medium.
- *General shape of petiole sinus.*—Half open.
- *Tooth at petiole sinus.*—Present.
- *Petiole sinus limited by veins.*—Absent.
- *Shape of upper lateral sinus.*—Open.
- *Depth of upper lateral sinus.*—Shallow.
- *Density of prostrate hairs between veins on lower surface of blade.*—Absent.
- *Density of erect hairs between veins on lower surface of blade.*—Absent.
- *Density of prostrate hairs on main veins on lower surface of blade.*—Absent.
- *Density of erect hairs on main veins on lower surface of blade.*—Absent.
- *Density of prostrate hairs on main veins on upper surface of blade.*—Absent.

*Autumn coloration of leaves.*—About Yellow-green 153D.

Upper surface:

*Color.*—About Yellow-green 147A.
*Surface texture.*—Smooth.
*Surface appearance.*—Semi-glossy.
*Goffering of blade.*—Present.

Lower surface:

*Color.*—About Yellow-green 146B.
*Anthocyanin coloration on main veins on lower leaf surface.*—Absent.
*Glossiness.*—Weak.
*Pubescence.*—Absent.
*Surface texture.*—Smooth.
*Surface appearance.*—Semi-glossy.

Petiole:

*Length of petiole.*—Long — approximately 9.63 cm.
*Length of petiole compared to middle vein.*—Slightly shorter.
*Density of prostrate hairs on petiole.*—Absent.
*Density of erect hairs on petiole.*—Absent.
*Shape of base of petiole sinus.*—U-shaped.

Buds:

*Shape.*—Slightly pointed.
*Size.*—Medium — approximately 4.0 mm by 6.0 mm.
*Position.*—Slightly held out (45° angle).
*Cane bud fruitfulness.*—Medium and distal fruitful.
*Time of bud burst.*—Early.

FLOWERS

General:

*Flower sex.*—Hermaphrodite.
*Length of first inflorescence.*—Medium.
*Position of first flowering node*—Fourth node.
*Number of inflorescences per shoot.*—Approximately 1.1 to 2.
*Date of full bloom.*—May 8, 2002.
*Time of bloom.*—Early.
*Size* (*diameter of fully open flower*).—Medium.

FRUIT

General:

*Ripening period.*—Medium — about 35 days ahead of Thompson Seedless.
*Use.*—Fresh market.
*Keeping quality.*—Medium.
*Disease resistance.*—Neither resistance nor susceptibility to diseases and pests has been observed in this cultivar.
*Shipping quality.*—Medium.
*Date of first harvest.*—Sep. 7, 2002.
*Solids-sugar.*—Medium — approximately 18%.
*Refractometer test.*—Approximately 20.0.
*Acid.*—Low — approximately 3.14 g/liter tartaric acid.
*Juice pH.*—Approximately 4.08.

Cluster:

*Bunch size* (*peduncle excluded*).—Medium.
*Bunch length* (*peduncle excluded*).—Intermediate — approximately 21.5 cm.
*Bunch width.*—Approximately 15.0 cm.
*Bunch weight.*—Medium — approximately 635.8 average weight per bunch.
*Bunch density.*—Loose.
*Number of berries.*—Approximately 163.
*Form.*—Conical.

Peduncle:

*Length of peduncle.*—Approximately 6.28 cm.
*Lignification of peduncle.*—Weak.
*Color.*—About Yellow-green 145B.

Berry:

*Size.*—Medium.
*Uniformity of size.*—Uniform.
*Berry weight.*—High — approximately 3.98 g.
*Shape.*—Elliptic — ovate.
*Presence of seeds.*—Rudimentary — approximately 4.7 mg.
*Cross section.*—Circular.
*Dimensions.*—Approximately 241 mm longitudinal axis by approximately 179 mm horizontal axis.
*Skin color* (*without bloom*).—About Greyed-yellow 160A.
*Coloration of flesh.*—Transparent greenish.
*Juiciness of flesh.*—Slightly juicy.
*Berry firmness.*—Firm.
*Particular flavor.*—None.
*Bloom* (*cuticular wax*).—Very weak.
*Pedicel length.*—Intermediate — approximately 6.98 cm.
*Berry separation from pedicel.*—Medium.
*Visibility of hilum.*—Slightly clear.

Skin:

*Thickness.*—Thick.
*Texture.*—Medium.
*Reticulation.*—Absent.
*Roughness.*—Absent.
*Tenacity.*—Free.

What is claimed is:

1. A new and distinct variety of grapevine plant named 'Sugratwentysix' as herein illustrated and described.

* * * * *